United States Patent [19]
DeLaurentis et al.

[11] Patent Number: 5,295,979
[45] Date of Patent: Mar. 22, 1994

[54] URINARY CATHETER AND SYSTEM

[75] Inventors: Mark DeLaurentis, Ocean Springs, Miss.; Kambiz Pourrezaei, Dresher, Pa.; Raymond L. Boxman, Herzliya, Israel; Richard B. Beard, Atco, N.J.

[73] Assignee: P & D Medical Coatings, Inc., Dresher, Pa.

[21] Appl. No.: 859,062

[22] Filed: Mar. 27, 1992

[51] Int. Cl.$^5$ ............... A61M 5/32; A61M 25/00
[52] U.S. Cl. .................................. 604/265; 604/328
[58] Field of Search ............... 604/93, 264, 265, 280, 604/327, 328

[56] References Cited

U.S. PATENT DOCUMENTS

| | | | |
|---|---|---|---|
| 2,900,979 | 8/1959 | Bishop | 604/327 |
| 4,232,677 | 11/1980 | Leibinsohn | 604/265 |
| 4,677,143 | 6/1987 | Laurin et al. | 604/265 |
| 4,840,625 | 6/1989 | Bell | 604/349 |
| 4,886,505 | 12/1989 | Haynes et al. | 604/265 |
| 4,933,178 | 6/1990 | Capelli | 604/265 |
| 5,057,094 | 10/1991 | Abbey | 604/327 |

Primary Examiner—Randy C. Shay
Attorney, Agent, or Firm—William H. Meise

[57] ABSTRACT

A urinary catheter and system includes a catheter with a drain lumen which is coated with oligodynamic metal and preferably arranged with a coating of a more noble metal for creating an iontophoretic galvanic couple, which drives antimicrobial ions into solution. The exterior of the catheter is also coated in a similar manner to inhibit microbes migrating toward the bladder along the outer surface of the catheter. The system includes a flow rate control device which may be a one-way valve, a filter or both. A collection bag is coupled to the control device. The interconnecting hoses, the flow rate control device(s) and the collection bag are also coated on the interior with oligodynamic metal, preferably silver, and also with a more noble metal, preferably platinum.

42 Claims, 5 Drawing Sheets urinary catheter and system

BACKGROUND OF THE INVENTION

This invention relates to urinary catheters and catheter systems generally, and more specifically to such catheters and other devices which are coated with metal to reduce microbial infection.

Four million urinary catheters are used yearly in the United States, and about 40 percent of patients develop urinary tract infections due to the use of the catheter. About 3.2 percent of the total number develop bacteriaemia (bacteria in the blood). Ten to twenty thousand people die each year, and about one billion dollars are expended to manage the complications arising from the use of urinary catheters and drainage systems. Clearly, any means which helps to reduce such infections may have a significant effect on the overall cost of medical services.

U.S. Pat. No. 3,598,127, issued Aug. 10, 1971 to Wepsic describes a catheter in which V-shaped grooves or chambers are provided, which contain antibacterial agents which diffuse through a permeable outer coating. Other patents such as U.S. Pat. No. 4,612,337, issued Sep. 16, 1986 to Fox, Jr. et al. describe various schemes for attaching or bonding antimicrobial agents to catheter materials. In general, such antimicrobial agents have a short half-life, and the microbes develop resistance to the agent.

U.S. Pat. No. 4,054,139, issued Oct. 18, 1977 to Crossley describes a catheter which embeds particles of "oligodynamic" (effective in small quantities) metals in a plastic matrix on the inner and outer surfaces of the catheter, to thereby inhibit microbial action. The matrix covers most of the surface of those metal particles and may envelop other particles completely. This arrangement, when used in a blood vessel, may produce an effect in preventing actual colonization of the surface by microbes, but may not be sufficient to kill or inhibit microbes migrating along the space between the exterior of the catheter and the skin, because of insufficient oligodynamic ion density, even though the space between the outside of the catheter and the skin which is available for migration of microbes is very small. However, the relatively large lumen required for use as a urinary catheter renders an arrangement such as that of Crossley essentially ineffective, for reasons described below.

U.S. Pat. No. 4,411,648, issued Oct. 25, 1983 in the name of Davis et al. describes an arrangement which uses an external voltage source to drive ions from a metal wire into fluid in the lumen of a urinary catheter. The ions then diffuse into the bladder. No attempt is made to prevent bacteria from moving along the outside of the catheter toward the bladder. The Davis et al. arrangement acts on bacteria or microbes moving in reflux from the exterior through the lumen, and also on those which are exiting from the bladder through the lumen.

U.S. Pat. No. 4,569,673, issued Feb. 11, 1986 in the name of Tesi, shows a pair of metal rings affixed on the exterior of a urinary catheter, with the rings connected to an external power source, for reducing microbial migration along the exterior of the catheter. Contamination through the lumen, as for example due to reflux, is not taken into account, nor is the possibility that, if microbes enter the bladder, they can colonize the exterior of the catheter at locations more distal than the rings.

All of the above patents describe devices which have metallic surfaces which are hydrophilic, and which confer protection against encrustation by proteins and minerals. Plastics are generally hydrophobic, thereby tending to increase the adhesion of bacteria and proteins.

U.S. Pat. No. 4,923,450 to Maeda, et al. describes a polymeric catheter into which silver-containing zeolite is impregnated as an antimicrobial. However, impregnation with zeolite decreases the tensile strength of the catheter.

A copending application entitled "Metallic-Surface Antimicrobial, Antithrombogenic Devices", filed concurrently herewith in the name of DeLaurentis et al., describes catheters, artificial blood vessel, valves or stents which are made from a combination of dissimilar metals which provide both antimicrobial and antithrombogenic properties. A catheter according to an aspect of the invention described in the DeLaurentis et al. application provides a conduit for access between a blood vessel or vas and the exterior of the body. The catheter includes a flexible tube which defines at least inner and outer surfaces. A layer or coating of a first metal (a metallization), supported by one or both of the inner or outer surfaces of the catheter, extends from near the point of entry into the vas to the distal end of the catheter. A coating of a second metal, dissimilar from the first metal, is supported by the same one of the inner or outer surfaces that supports the coating of the first metal. The coating of the second metal is contiguous with, and in galvanic contact with the coating of the first metal, thereby forming an iontophoretic (ion-pumping) galvanic couple. The second metal coating extends proximally from about the point of entry of the catheter into the vas to a location outside the body. Thus, the two metals forming the couple are exposed in different regions, and the antithrombogenic and antimicrobial properties occur in different regions. In another embodiment of the DeLaurentis et al. invention, the inside of the catheter is coated with two galvanically connected dissimilar metals, and the junction therebetween is located at a point sufficiently remote from the distal end so that it is ordinarily not reached by blood. The two dissimilar metals may include an oligodynamic metal such as silver and a more noble metal such as platinum. Stents, valves and artificial blood vessels as described by DeLaurentis et al. similarly include a junction of dissimilar metals, one of which may be oligodynamic metal and the other a more noble metal. In particular, the less noble or oligodynamic metal is located on that surface or surfaces of the device which, when in use, are adjacent to solid body tissue, while in all cases the more noble metal is adjacent the principal path for blood flow for thereby reducing clot formation.

SUMMARY OF THE INVENTION

A urinary catheter according to the invention is coated on both the interior (the lumen) and the exterior with a layer of exposed metals selected to provide iontophoretic (ion-pumping) action by which oligodynamic metal ions are driven into solution for inhibiting microbial activity at locations adjacent to the exterior of the catheter, so as to inhibit the migration of microbes into the urethra and bladder along the exterior, and a similar coating along the interior of the lumen inhibits microbes passing therethrough from the bladder. A urinary catheter system according to the invention uses the abovedescribed catheter in conjunction with a reflux reduction device such as a one-way valve or a flow rate controller, a collection receptacle and interconnecting tubes, some or all of which are made from or coated with metals for inhibiting microbial activity.

DESCRIPTION OF THE DRAWING

FIG. 4b is a cross-section of a hollow glass sphere which may be used within the filter of FIG. 4a;

DESCRIPTION OF THE INVENTION

Experimentation with nutrient broths, which is considered a worst-case condition, has revealed that inhibition of microbes requires about 25 to 50 square millimeters (mm) of silver surface per milliliter (ml) of broth when that silver surface is not associated with a galvanic couple providing iontophoretic action, and about half that amount of surface in the presence of a galvanic couple. Simple geometric considerations therefore limit the maximum diameter of the lumen of a catheter with a simple silver coating to about 0.2 mm, and about 0.3 mm in the presence of a couple. Such lumen diameters are inadequate for the flow rates which are expected in urinary systems, especially at the time of initial catheterization, when the flow rates may be high. A larger lumen must be provided. The larger lumen, however, allows reflux of collected urine from the collection receptacle or bag toward the bladder in the not uncommon event that the collection receptacle is tilted while raised higher than the patient. If the collected urine were sterile, the reflux would not have injurious consequences. However, collected fluids may remain in the collection receptacle for days, with some of the material being removed periodically to prevent overfilling. The collection receptacle is at room temperature. While urine is not an ideal medium for microbial growth, the temperature and long growth interval conditions may allow colonization of the interior of the collection receptacle and substantial microbial densities in the fluid, which make reflux a serious matter. A catheter system according to an aspect of the invention inhibits the migration of microbes along the exterior of the catheter into the urethra and bladder, and also inhibits microbes flowing through the catheter system and reposing in the collection receptacle. Further, in another embodiment of the invention, reflux is impeded by a device for restricting flow in one direction (a valve) or by a bilateral flow rate restriction device.

Figure 1:
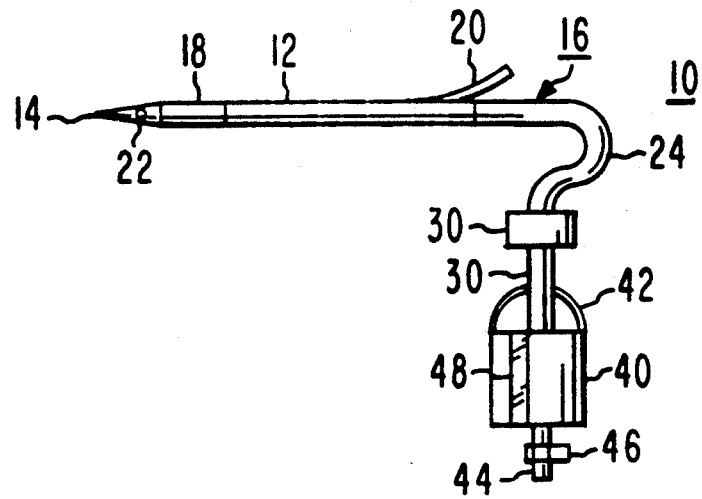
FIG. 1 is an overall view of a simplified urinary catheter system according to the invention, including a catheter, reflux reducing device, and collection receptacle or bag.

In FIG. 1, a catheter system 10 includes an elongated catheter 12 defining a distal end 14 and a proximal end designated generally as 16. Catheter 12 includes a retention balloon 18, illustrated in its deflated state, which communicates by way of an inflation lumen (not illustrated in FIG. 1) with an inflation connector 20. A main lumen (not illustrated in FIG. 1) extends from a distal aperture 22 to proximal end 16 of the catheter, at which it connects to a drain tube 24. Drain tube 24 extends to a reflux avoidance device designated 30, which is described in more detail below. A further tube 32 extends from reflux avoidance device 30 to a collection container in the form of a closed bag 40, which includes a handle or strap 42 for hanging, and also includes a drain tube 44 and drain tube shutoff clamp 46. A transparent window 48 in the side of container 40 is associated with a scale (not illustrated in FIG. 1).

Figure 2A:
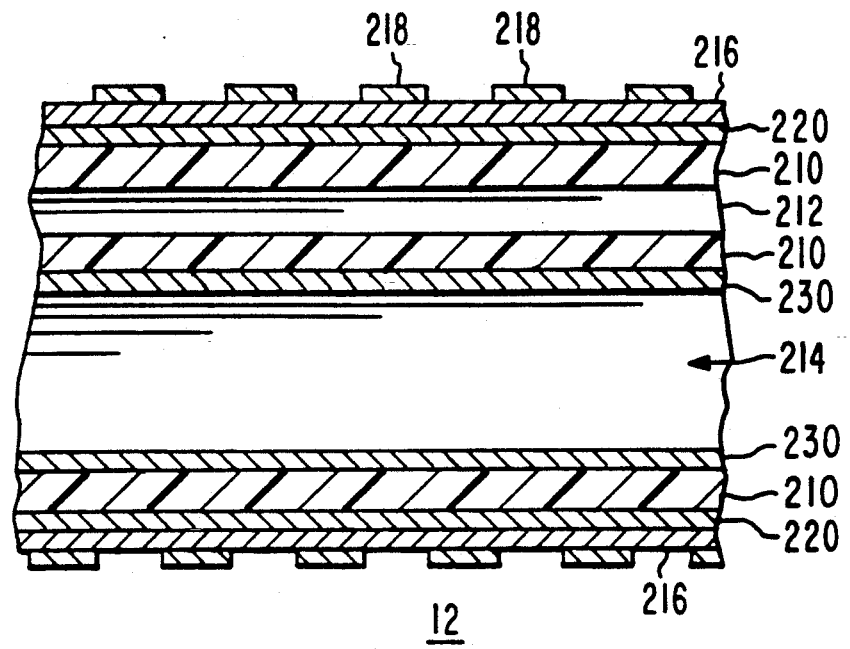
FIG. 2a is a cross-sectional view of a portion of the urinary catheter of FIG. 1, illustrating metallized surfaces.
Figure 2B:
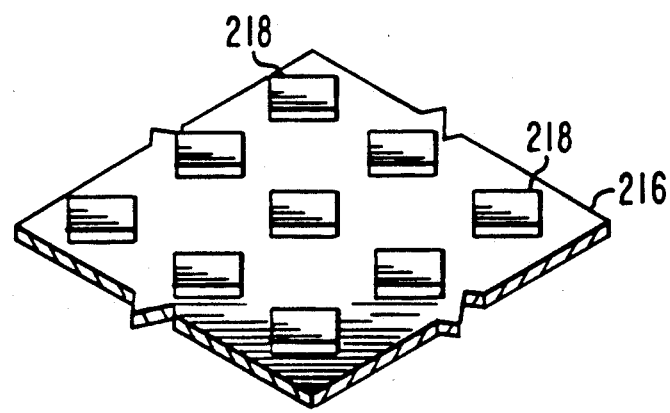
FIG. 2b is a perspective or isometric view of the exterior surface of the catheter of FIG. 2a, and FIG. 2c is a cross-section of a catheter with another metallization pattern.

FIG. 2a is a cross-sectional view of catheter 12 of FIG. 1, illustrating a body 210 made from a polymer such as tetrafluoroethylene, defining a balloon inflation lumen 212 and a main drainage lumen 214. Inflation lumen 212 communicates with balloon 18 and with inflation port or connection 16 of FIG. 1, and drain lumen 214 communicates with distal aperture 22 and with drain tube 24 of FIG. 1. As illustrated in FIG. 2, the exterior surface of catheter 12 is covered with exposed metallic coatings. A continuous layer 216 of a first metal is covered with mutually separated dots or spots 218 of a second metal. The exterior surfaces of those portions of layer 216 which do not lie under dots 218 are exposed, and the surfaces of dots 218 are also exposed. FIG. 2b is a perspective or isometric view of a possible shape for such dots or spots, but the exact shape is not of great significance. In accordance with an aspect of the invention, the second metal is an oligodynamic metal such as silver, while the partially exposed underlying metal layer is a more noble metal such as platinum. This combination of metals sets up a galvanic couple which promotes iontophoresis, or the generation of ions. In the arrangement as described, silver ions are generated at dots 218 when the catheter is in place, since the surrounding urine and mucous fluids act as an electrolyte through which minute amounts of electrical current may flow. These silver ions go into solution, and, at a sufficient density, inhibit microbial growth.

The surfaces of retention balloon 18 of FIG. 1 are also covered with exposed metal surfaces as described above. Most catheter balloon materials are not very elastic, and the balloons are might more properly termed "bags", but the "balloon" terminology is well established. The retention balloon, the outer surface of the catheter in the distal region, and the lumen in the distal region, and drain aperture 22, preferably are all coated with interconnected exposed metal, so that no uncoated regions remain where microbial colonization could occur.

As mentioned in copending patent application Ser. No. 07/859,063 entitled "Method for Fabrication of Metallized Catheters", filed Mar. 27, 1992 in the name of Pourrezaei et al., the corrosion of exposed silver in a galvanic couple such as that described in conjunction with FIGS. 2a and 2b could, if the silver layer were the underlying exposed layer 216 and the dots 218 were platinum, result in disconnection of the exposed silver from the platinum dots, thereby reducing the amount of silver connected to the galvanic couple, and reducing the activity of the device even though exposed silver remains. The arrangement as illustrated in FIGS. 2a and 2b allows the galvanic couple to operate until such time as the silver dots are completely dissolved. An initial corrosion rate of about ½ micron per week is expected, which rate decreases as the concentration of ions in solution increases, so the overall corrosion rate should not exceed about ½ micron per week, and dots which are a few microns thick should be more than enough for ordinary use.

As also indicated in the abovementioned Pourrezaei et al. application, the adhesion of some metals to underlying polymers may not be adequate for prolonged use in the presence of watery fluids, because the water tends to migrate through pores and cracks in the metallic coatings to attack and loosen the attachment to the base material. As therein described, an improvement is achieved by applying a first or base coating of silver for good adhesion, following which one or more additional layers may be applied, with the outermost "incomplete" layer (corresponding to dots 218 of FIGS. 2a and 2b) being silver or other oligodynamic metal, and the outermost "complete" layer (corresponding to partially exposed layer 216 of FIGS. 2a and 2b) being platinum or other metal more noble than the oligodynamic layer. In FIG. 2a, layer 220 is an adhesion-enhancing silver layer, which is completely covered by platinum layer 216. Additional layers of silver, or of alternating layers of silver and platinum, or of other metals, may be interposed between layers 216 and 220, for filling pores and cracks.

The surface of drain lumen 214 of catheter 12 of FIG. 2a is coated with a layer 230 of silver, which is connected at proximal and distal ends of the lumen to a more noble metal, as by connection to exterior platinum layer 216. Thus, silver layer 230 is part of a galvanic couple, for iontophoresis. Ideally, a pattern of silver dots is also applied over an underlying platinum layer on the surface of the lumen, but the additional plating steps may be a manufacturing effort which is not be justified by a corresponding increase in the oligodynamic ion density. This is especially true, considering that the desired ratio of silver surface to volume for complete inhibition throughout the volume of the lumen cannot be achieved for a lumen diameter greater than about 0.2 mm when the walls alone are relied upon. The silver ion density near the lumen surface or walls may, however, be sufficiently high to prevent colonization of the surface of the lumen.

The catheter, and other devices described herein, may be made by conventional methods, or by the improved methods described in the abovementioned copending Pourrezaei et al patent application Catheters or other devices according to an aspect of the invention described in the aforementioned Pourrezaei et al. application include those in which plural layers of metals are applied to the surfaces of the device, which tend to close minuscule cracks or pores through which corrosion may attack the underlying support structure. The catheter support may be made from TEFLON (polytetrafluoroethylene) or from other materials. In some embodiments or avatars, the initial layer of material is preferably silver, applied following preparation steps which may include cleaning, drying and etching. In some embodiments, succeeding layers of metal completely cover the initial layer, and are also of silver. The succeeding layers are deposited after deposition of the prior layer has ceased, and such succeeding layers have unexpectedly been found to tend to reduce the incidence of microscopic pores or cracks and to therefore be less prone to delamination. The succeeding layers are preferably of mutually different metals between layers. In a particular avatar, in which the exposed metals are silver (or other oligodynamic metal) and platinum (or other more noble metal), the exposed silver layer lies over a portion of the platinum layer, to thereby prevent corrosion of the silver layer near the junction of the metals from electrically disconnecting portions of the silver layer from the platinum. Fabrication methods include deposition of successive layers by means of sputtering a continuous run of catheter material in a longitudinal array of cylindrical (or other) magnetrons or magnetron sections or segments, in which each magnetron or section thereof applies one layer of the coating over the coating applied by the preceding magnetron or section of the array. The magnetrons or sections may be energized and deenergized in a temporal pattern associated with the progress of the catheter material through the array, to thereby cover or expose particular layers at particular positions along the length of the catheter material. In some embodiments of the invention, a first layer of electrically conductive material is deposited by electroless methods, following which additional layers may be applied by conventional electrolytic deposition. An electroless application method may be used for depositions in a lumen of a catheter. An electroless method according to the Pourrezaei et al. invention includes preparation steps which may include ultrasonically cleaning the surface with a solution of isopropyl alcohol, then drying the surface with a stream of dry gas, and etching the surface with a solution of sodium naphthalene in diethylene glycol dimethyl ether, commercially available as CHEM-GRIP TREATING AGENT from Norton Performance Plastics of Wayne, N.J. After the preparation steps, the inner surface is acidified and neutralized by hydrochloric acid, sensitized with a solution of $SnCl_2/HCl$, and rinsed. The actual electroless plating is accomplished by a plating solution including $AgNO_3$, sodium dodecylbenzenesulfonate, and ammonia solution, with acetic acid added for pH adjustment, together with a reducing solution of $N_2H_4:H_2O$(hydrazine hydrate). Each of the above steps may be separated from the next by rinsing and drying steps.

Figure 2C:
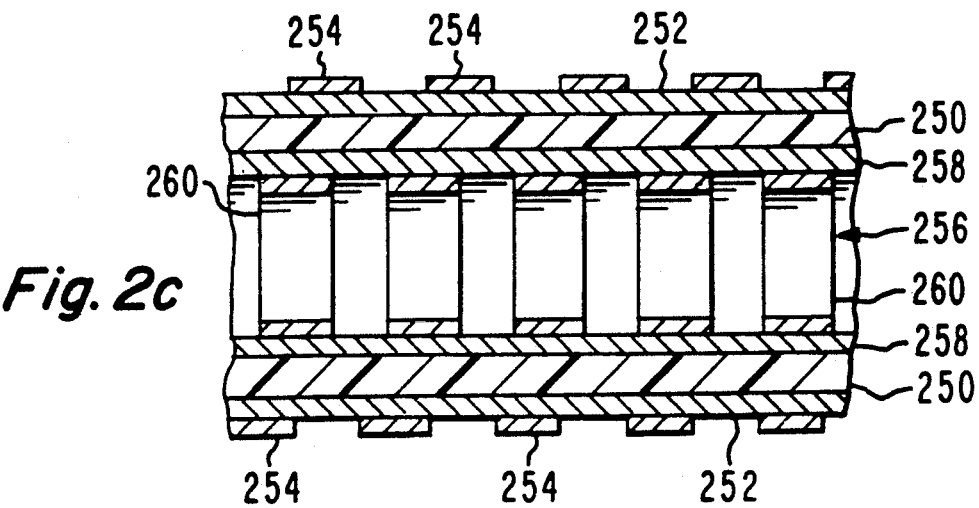

FIG. 2c is a cross-section of a portion of a catheter according to another aspect of the invention, illustrating a polymer body 250, with a continuous coating 252 of platinum on the exterior surface, and with additional annular rings 254 of silver extending about the body. Similarly, the drain lumen 256 has a continuous coating 258 of platinum, over which rings 260 of silver are applied. The patterns are readily accomplished by masking.

It is believed that, in order for the iontophoresis to be fully effective, portions of at least three mutually adjacent patches or rings must reside within the urethra. Thus, one ring or patch or silver, with at least a portion of a platinum patch at the distal end and a portion of another platinum patch at the proximal end lying within the urethra, would be sufficient. Preferably, a large number of patches would reside therein.

Figure 3:
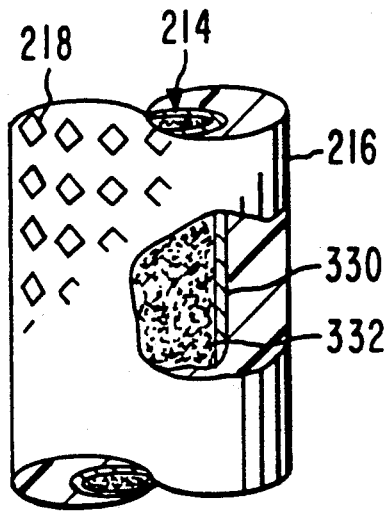
FIG. 3 illustrates a portion of a catheter tube, partially cut away to show the presence of metal wool within the lumen.

In accordance with an aspect of the invention, the surface-to-volume ratio is improved as illustrated in FIG. 3 by making the exposed surface 330 of a lumen 214 of platinum, and by filling the lumen with silver wool 332. The silver wool makes contact with the platinum walls of the lumen at numerous points, thereby generating the desired galvanic action, and the density of the silver fibers can be selected to provide the desired surface-to-volume ratio. Naturally, the metal wool could also be made from platinum, and the lumen walls from silver, or the wool could be an intermixture of oligodynamic and more noble metal fibers. The preferred arrangement includes lumen walls of exposed silver, together with metal wool of intermixed silver- and platinum-surface fibers.

Figure 4A:
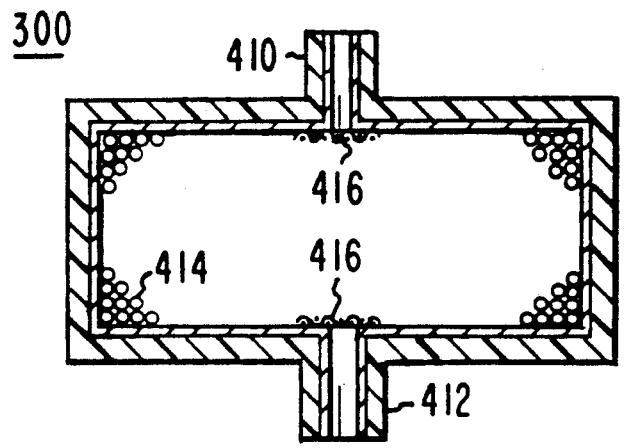
FIG. 4a is a simplified side elevation view, partially cut away to reveal interior details, of a flow rate control device according to the invention, in the form of a filter.
Figure 4B:
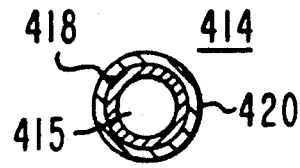

FIG. 4a is a side cross-section of a flow restricting device 300 which may be used in place of device 30 of FIG. 1. In FIG. 4a, a drum-shaped container includes input and output hose connectors 410 and 412, respectively. The inner surface of container 300 is coated with exposed silver, which coating may be of multiple layers, as mentioned. The interior of device 300 is filled with a large number of small particles or spheres 414, the exposed surfaces of which are an intermixture of silver and platinum, retained in place by screens 416. The simplest arrangement is to fill the interior with a mixture of silver and platinum powders, thereby creating innumerable small passages, each with an effective diameter less than 0.2 mm. Each such small passage alone has excessive resistance to liquid flow, but the large number of such passages in parallel, together with the large diameter of device 300, provide sufficient flow. Material may be conserved by filling the interior of device 300 with small glass spheres, some of which are coated with silver, and others of which are coated with platinum. FIG. 4b is a cross-section of such a sphere 414, illustrating an empty center 415 surrounded by a glass bubble 418, the exterior surface of which is coated with a layer 420 of metal. In operation, device 300 provides a relatively high flow rate, but also interposes a delay from the time that flow begins at one side until it emerges from the other side. This delay allows the position of the container to be readjusted before reflux flow reaches the patient. At the same time, the high ion density within the small passages of the device tends to inhibit microbes within the flow, and in ordinary use will tend to increase the ion density within container 40, thereby tending to minimize microbial growth therein.

Figure 5A:
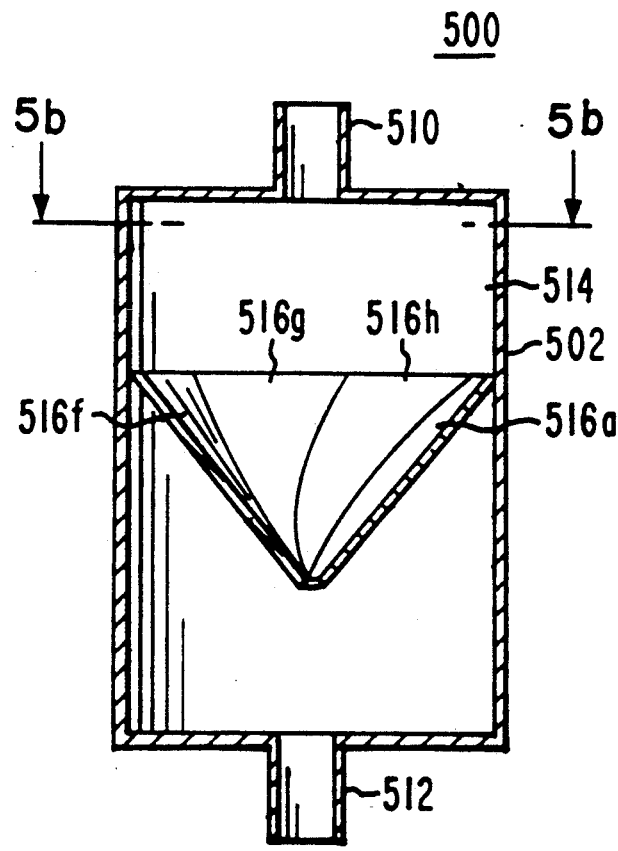
FIG. 5a is a simplified side cross-sectional view of a one-way valve which may be used with, or instead of, the filter of FIG. 4.
Figure 5B:
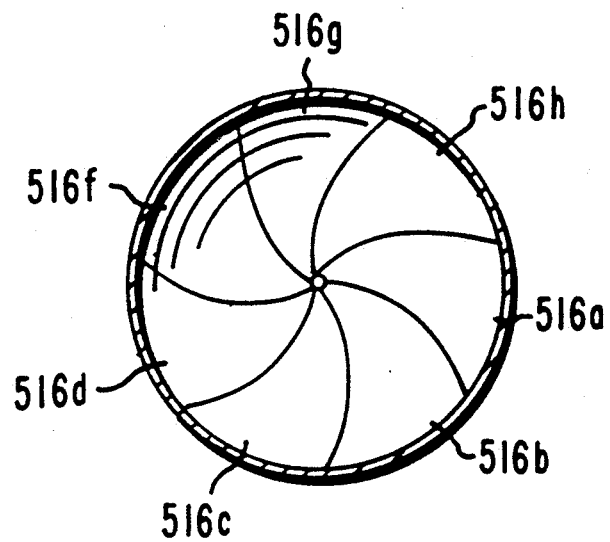
FIG. 5b is an end view of the control flaps thereof.

In FIG. 5a, a one-way valve 500 which may be used instead of, or in conjunction with, filter 300 of FIG. 4, includes a body 502 defining a cylindrical center region 514. Within center region 514, a plurality of thin, flexible control vanes or flaps 516a through 516h are attached at one end to the wall of body 502 and extend, partially overlapping each other, to the center. FIG. 5b is an axial view of the flaps, looking along section lines 5b–5b of FIG. 5a. For flow from input port 510 toward output port 512, each flap is supported essentially only at its attachment to body 502, so each flap can deflect downward to allow flow. Retrograde flow is impeded by the flaps, which are prevented from deflecting in the flow direction by the support of adjacent flaps. In accordance with an aspect of the invention, the interior walls of body 502, and each of the flaps 516, is coated with one or more metals, at least one of which is oligodynamic. Except during heavy flows during initial catheterization, the flow is a trickle which flows in a thin film over the interior surfaces of the valve, and in which microbial inhibition will therefore occur with a simple oligodynamic metal coating. To enhance activity, the major surfaces of the flaps may be coated with silver, and the edges of the flaps in the overlapping regions may be coated with platinum, to provide an iontophoretic couple. The flaps are relatively narrow near the center of the structure, as well as being thin and flexible. Consequently, each flap, at a location most remote from its support by body 502, has little structural strength, and even in a mutually supporting arrangement may deflect in the event of a substantial reflux fluid pressure.

Figure 6:
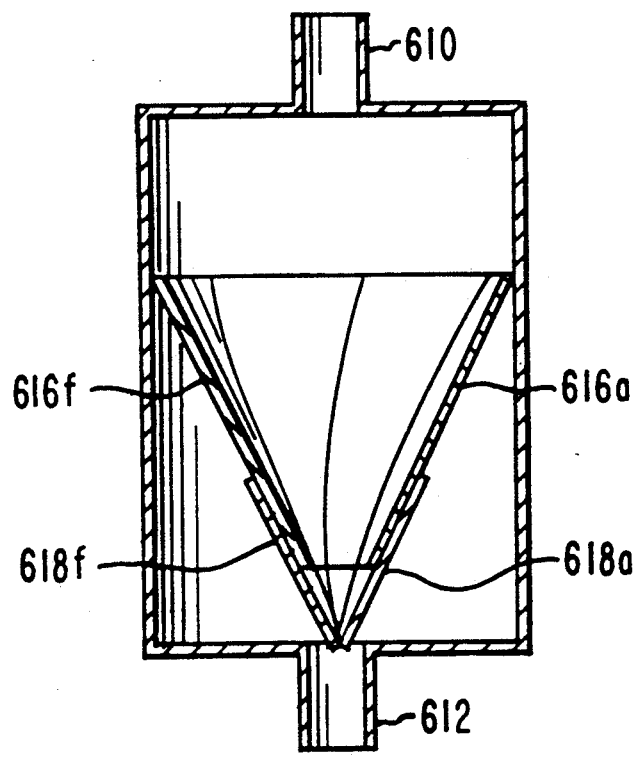
FIG. 6 is a simplified side cross-sectional view of a modification of the one-way valve of FIGS. 5a and 5b, modified by the addition of stiffened flap ends.

FIG. 6 is a simplified side cross-section of another one-way flow valve, generally similar to that of FIG. 5a and 5b. In FIG. 6, body 602 supports valve flaps 616 as described above, but the end of each valve flap 616 at a location most remote from its support by body 502 is truncated, and a more rigid flap portion 618 extends toward the center of the structure from the point of truncation. Thus, the relatively weak tips of the flaps are replaced by stronger, more rigid structures for added resistance to reflux pressure.

Figure 7A:
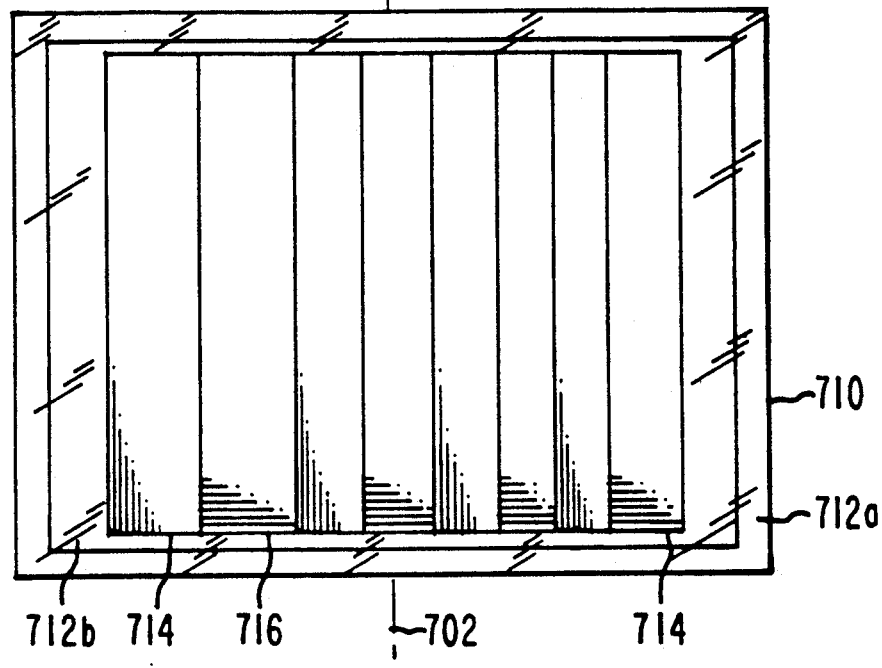
FIG. 7a is a simplified view of a collection receptacle according to the invention in a partially completed form, illustrating the interior metallization pattern.

FIG. 7a is a simplified view of an unfolded or partially manufactured urinary catheter collection bag according to the invention, which may be used in the arrangement of FIG. 1. The side of sheet 710 visible in FIG. 7a is the side which, after folding along fold line 702 and peripheral sealing during fabrication, lies within the collection bag. In FIG. 7a, a rectangular sheet 710 of transparent or translucent polymer includes an outer margin region 712a and 712b, where no metallic coating is provided. Region 712a is a region in which sealing takes place at a later step of fabrication, and region 712b is a region which is later available as a window, for ascertaining the level of the collected fluid. According to an aspect of the invention, the main portion of the visible side of sheet 710 is coated with exposed metal. As described in more detail in the abovementioned copending DeLaurentis et al. and Pourrezaei et al. applications, the coating may constitute a layer 714 of a first metal which extends over the entirety of the metallized region, over portions or patches of which a second layer 716 of metal is applied, to result in exposed portions of two metals. The preferred second exposed metal is an oligodynamic metal such as silver, and the first metal is a more noble metal such as platinum.

The metal pattern in FIG. 7a may be deposited with the aid of a first mask for depositing the underlying layer of metal 714 over the entire surface except for the outer margin regions 712a and 712b, followed by a second mask which defines the second patches, and which prevents deposition of the second metal layer 716 on the outer margin area. The first masking operation may be dispensed with in conjunction with the deposition of first metal layer 714, whereby the deposition takes place all the way to the edge of the sheet, in which case sealing is accomplished by folding over the edges, so that a portion of the uncoated "outer" surface forms an effective margin, and those uncoated margin portions of the outer surface may be sealed together. Sheet 710 of FIG. 7a may be made from a thermoplastic material, which is masked and coated as described above. Assuming that the marginal regions 712a and 712b, as illustrated in FIG. 7a, are not coated with metal, sheet 710 is folded along its fold line 702, and the input and output ports are then placed in position. Heat and pressure are applied to sealing surface 712a, thereby sealing the edges of the container, and also sealing the container to the input and output ports. During sealing, some heat is also applied to region 712b while a slight overpressure of air is applied to the ports, to allow plastic flow in region 712b, which allows the volume of the completed receptacle to increase. The input and drainage ports may be molded in known fashion with an almond-shaped or tapered cross-section where they enter and seal to the bag, and with round cross-section at the free ends, to thereby allow coupling to standard connectors.

Figure 7B:
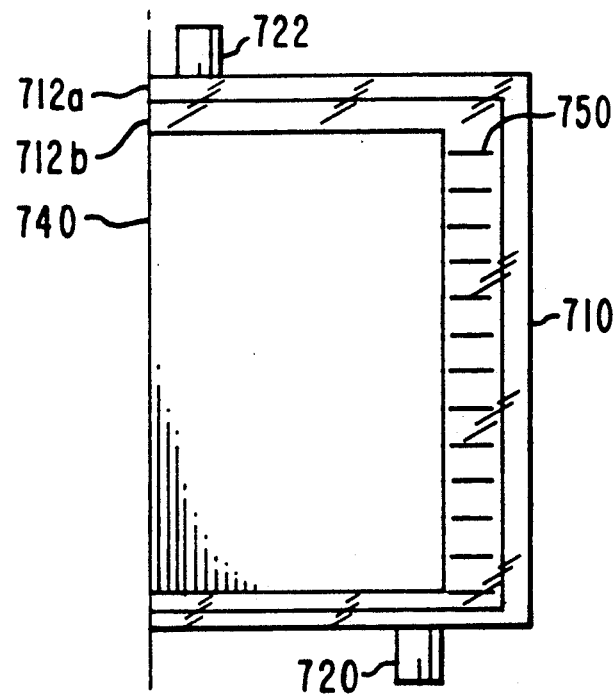
FIG. 7b illustrates the receptacle after folding and sealing.

FIG. 7b is a view of the exterior of the collection receptacle of FIG. 7a after folding, adding input and drainage ports, and sealing. As illustrated, the central region 740 is opaque because of the application of metallization layers 714 and 716 of FIG. 7a. A scale 750 may be printed on the outside of the collection receptacle, or preferably the scale markings are metallic coating applied to the interior as part of the same step by which one of the first or second metal coatings 714, 716 is applied, to thereby eliminate one manufacturing step.

In accordance with another aspect of the invention, all the interconnecting hoses, such as hoses 24 and 32 of FIG. 1, are coated on the inside surface, i.e. the surface of the drain lumen, with a layer of oligodynamic metal such as silver, which is in communication with the coatings of the adjacent device. Thus, a continuous metallic antimicrobial coating extends through the drain lumen from the distal end of catheter 12 of FIG. 1, through the catheter, hose 24, filter 30 of FIGS. 1 and 4a and or one-way valve 500 of FIG. 5, and through hose 32 of FIG. 1, and into receptacle 40. This continuous coating preferably includes an oligodynamic metal, and is preferably rendered more active by iontophoresis provided by a galvanic couple. The most preferred arrangement includes the abovementioned continuous coating through the drain lumen, together with a metallic coating on the exterior surface of the catheter itself, as described in conjunction with FIGS. 2a and 2b, to inhibit migration of microbes along the outer surface of the catheter.

The metallic coatings of the various surfaces may be made by conventional methods or by the methods described in the aforementioned Pourrezaei et al. application. The dots, or other patterns on the exterior surface, may be made by simple masking techniques. Patterns on the interior surfaces of lumens may be made by electrodeposition from electrodes having the desired pattern, as for example an interconnected pattern may be electrodeposited by a metallic screen.

In order to avoid the possibility of introduction of microbes into the interior of a hose, filter, valve or bag, the entire drain system, including the catheter if desired, can be assembled at the factory and sterilized after assembly by heat, radiation, or in any other fashion. Since there is no need for opening the closed system prior to use, there is no opportunity for ingress of microbes prior to catheterization such as might occur if the system had to be assembled from separate elements and hoses. The catheter system as described should remain free of active microbe colonies longer than other systems, thereby reducing the occurrences of infections with their complications, and also reducing the need for additional, replacement catheter systems, and the risks involved in recatheterization.

Other embodiments of the invention will be apparent to those skilled in the art. In particular, a one-way valve such as that of FIG. 5 may be used together with a flow rate reducing filter such as that of FIG. 4a. While silver has been described as the exposed oligodynamic metal which is corroded to produce microbe-inhibiting ions, other metals such as aluminum are known to produce a like effect. When used for draining bile from the bile ducts into the duodenum, a catheter coated in a manner such as that described may retard blockage by inhibiting the microbial growth which converts bile into an adhesive substance. While a tetrafluoroethylene substrate material has been described, other polymeric materials such as silicone may be used.

What is claimed is:

1. A catheter defining inner and outer surfaces and distal and proximal ends, said catheter comprising:
a smooth, flat continuous layer of a first metal extending over at least one of said inner and outer surfaces, said continuous layer of first metal extending from a point on said catheter to said distal end, said layer underlying a discontinuous smooth, flat layer of a second metal, dissimilar to said first metal, to thereby form contiguous exposed flat patches of said first and second dissimilar metals.

2. A catheter according to claim 1 wherein said continuous layer of first metal extends over both of said inner and outer surfaces.

3. A catheter according to claim 1, wherein said first metal is an oligodynamic metal.

4. A catheter according to claim 3, wherein said second metal is more noble than said oligodynamic metal.

5. A catheter according to claim 1 wherein said catheter defines a longitudinal axis, and said patches are in the shape of coaxial annular rings.

6. A catheter according to claim 1 wherein said patches are in the shape of dots.

7. A catheter according to claim 1, wherein said patches are dimensioned so that at least portions of three mutually adjacent patches can occupy a region which, when said catheter is in use, lies within a urethra.

8. A catheter according to claim 1, further including a flow restriction device coupled to the proximal end of said catheter, and a container coupled to the end of said flow restriction device remote from said catheter.

9. A catheter according to claim 8, wherein at least one of said flow restriction device and said container include interior surfaces with exposed dissimilar metals.

10. A catheter according to claim 9, wherein said container is fabricated from a translucent or transparent polymer material, and said dissimilar metals form a coating on a first portion of said interior surfaces of said container, whereby a second portion of said translucent or transparent polymer material forms a window for viewing the contents of said container.

11. A catheter according to claim 9 wherein at least one of said dissimilar metals coats a portion of said interior surface of said container in a pattern comprising scale markings indicative of the volume of liquid contained in the container when the liquid level is at a scale marking.

12. A catheter according to claim 9, wherein said dissimilar metals associated with said container include an oligodynamic metal and a metal more noble than said oligodynamic metal.

13. A catheter according to claim 9 wherein both said flow restriction device and said container include interior surfaces with exposed dissimilar metals.

14. A catheter according to claim 13, wherein said dissimilar metals associated with said flow restriction device include an oligodynamic metal and a metal more noble than said oligodynamic metal.

15. A catheter according to claim 1 wherein said dissimilar metals associated with said filter include an oligodynamic metal and a metal more noble than said oligodynamic metal.

16. A catheter according to claim 8, wherein said flow restriction device includes a filter, including filter elements of mutually dissimilar metals.

17. A catheter according to claim 8, wherein said flow restriction device includes a one-way valve, which one-way valve includes interior surfaces with exposed dissimilar metals.

18. A urinary catheter arrangement, comprising:
a catheter including a distal end, a proximal end, and inner and outer surfaces, said catheter including a continuous layer of a first metal extending over at least one of said inner and outer surfaces, said continuous layer of first metal extending from a point on said catheter to said distal end, said laxer of first metal underlying a discontinuous layer of a second, dissimilar metal to thereby define contiguous exposed patches of said first and second dissimilar metals;
a flow restriction device including an input port and an output port, the exposed interior surfaces of which flow restriction device include an oligodynamic metal;
a container including at least an input port, the exposed interior surfaces of which container include an oligodynamic metal;
first flow coupling means coupled to said proximal end of said catheter and to said input port of said flow restriction device for allowing flow therebetween, said first flow coupling means including exposed interior surfaces of oligodynamic metal; and
second flow coupling means coupled to said output port of said flow restriction device and to said input port of said container for allowing flow therebetween, said second flow coupling means including exposed interior surfaces of oligodynamic metal.

19. A catheter according to claim 18, wherein at least one of said flow restriction device and said container include interior surfaces with exposed dissimilar metals, one of which is said oligodynamic metal.

20. A catheter according to claim 19, wherein the other one of said dissimilar metals is a metal more noble than said oligodynamic metal.

21. A catheter according to claim 19, wherein both said flow restriction device and said container include interior surfaces with exposed dissimilar metals.

22. A catheter according to claim 21, wherein said dissimilar metals associated with both said flow restriction device and said container include said oligodynamic metal and a metal more noble than said oligodynamic metal.

23. A catheter according to claim 18, wherein said flow restriction device includes a filter, including filter elements of mutually dissimilar metals.

24. A catheter according to claim 18, wherein said flow restriction device includes a one-way valve, which one-way valve includes interior surfaces with exposed dissimilar metals.

25. A catheter according to claim 24, wherein said dissimilar metals associated with said one-way valve include an oligodynamic metal and a metal more noble than said oligodynamic metal.

26. A urine collection container arrangement, comprising:
a container including deformable walls defining inner and outer surfaces, and also including input and drain orifices;
a layer of a first metal extending over a portion of said inner surface of said container;
a layer of a second metal, dissimilar to said first metal, extending over a portion of said layer of a first metal on said inner surface of said container, whereby said second metal is exposed to the inside of said container, and said first metal is exposed in those regions not covered by said second metal said first and second layers of metal being in physical and electrical contact.

27. A container according to claim 26, wherein said first metal is an oligodynamic metal.

28. A container according to claim 27, wherein said second metal is more noble than said oligodynamic metal.

29. A container according to claim 26, wherein said deformable walls of said container are fabricated from a translucent or transparent polymer material, and said dissimilar metals together form a coating on a first portion of said interior surfaces of said container, whereby a second portion of said translucent or transparent polymer material forms a window for viewing the contents of said container.

30. A container according to claim 29 wherein at least one of said dissimilar metals coats a portion of said second portion of said interior surfaces of said container in a pattern comprising scale markings indicative of the volume of liquid contained in the container when the liquid level is at a scale marking.

31. A container arrangement according to claim 26, further including a catheter defining inner and outer surfaces and distal and proximal ends, said catheter comprising:
a continuous layer of metal extending over at least one of said inner and outer surfaces, said continuous layer of metal extending from a point on said catheter to said distal end, said layer containing contiguous exposed flat patches, each of said exposed flat patches including at least one of first and second dissimilar metals.

32. An arrangement according to claim 31, wherein said continuous layer of metal extends over both of said inner and outer surfaces.

33. An arrangement according to claim 32, wherein said first metal is an oligodynamic metal.

34. An arrangement according to claim 33, wherein said second metal is more noble than said oligodynamic metal.

35. An arrangement according to claim 31, wherein said patches are in the shape of annular rings.

36. An arrangement according to claim 31 wherein said patches are in the shape of dots.

37. An arrangement according to claim 31, wherein said patches are dimensioned so that at least portions of three mutually adjacent patches can occupy a region which, when said catheter is in use, lies within a urethra.

38. An arrangement according to claim 31, further including a flow restriction device coupled between said the proximal end of said catheter and said input port of said container.

39. An arrangement according to claim 38, wherein said flow restriction device includes interior surfaces with exposed dissimilar metals.

40. An arrangement according to claim 39, wherein said dissimilar metals associated with said flow restriction device include an oligodynamic metal and a metal more noble than said oligodynamic metal.

41. An arrangement according to claim 38, wherein said flow restriction device includes a filter, including filter elements of mutually dissimilar metals.

42. An arrangement according to claim 38, wherein said flow restriction device includes a one-way valve, which one-way valve includes interior surfaces with exposed dissimilar metals.

* * * * *